(12) United States Patent
Mine

(10) Patent No.: US 6,374,674 B1
(45) Date of Patent: Apr. 23, 2002

(54) ULTRASONIC DIAGNOSTIC APPARATUS

(75) Inventor: Yoshitaka Mine, Tochigi-ken (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/401,969

(22) Filed: Sep. 23, 1999

(30) Foreign Application Priority Data

Oct. 14, 1998 (JP) ............................................ 10-292150

(51) Int. Cl.$^7$ ............................ G01N 29/04; A61B 8/00
(52) U.S. Cl. ............................... 73/606; 73/620; 73/626; 600/443; 600/447
(58) Field of Search ......................... 73/606, 602, 625, 73/621, 607, 626, 620, 618, 624, 627, 634; 367/7; 128/660; 600/443, 444, 447

(56) References Cited

U.S. PATENT DOCUMENTS

| | | | | |
|---|---|---|---|---|
| 4,596,145 A | * | 6/1986 | Smith et al. .................... | 73/626 |
| 4,694,434 A | * | 9/1987 | Von Ramm et al. ............. | 367/7 |
| 5,060,651 A | * | 10/1991 | Kondo et al. ................... | 73/626 |
| 5,142,649 A | * | 8/1992 | O'Donnell ....................... | 367/7 |
| 5,282,471 A | * | 2/1994 | Sato ............................... | 128/916 |
| RE34,566 E | * | 3/1994 | Ledley ........................... | 600/443 |
| 5,546,807 A | | 8/1996 | Oxaal et al. .................... | 73/606 |
| 5,560,360 A | * | 10/1996 | Filler et al. ................... | 600/408 |
| 5,928,151 A | * | 7/1999 | Hossack et al. ............. | 600/443 |
| 6,042,546 A | * | 3/2000 | Bae .............................. | 600/447 |
| 6,186,948 B1 | * | 2/2001 | Kamiyama et al. ......... | 600/443 |

OTHER PUBLICATIONS

E. D. Light, et al. Progess in Two-Dimensional Arrays for Real-Time Volumetric Imaging Ultrasonic Imaging 20, 1–15 (1998).

* cited by examiner

Primary Examiner—Hezron Williams
Assistant Examiner—Jacques Saint-Surin
(74) Attorney, Agent, or Firm—Oblon, Spivak, McClelland, Maier & Neustadt, P.C.

(57) ABSTRACT

An ultrasonic diagnostic apparatus wherein a three dimensional space is scanned by ultrasonic beams and echo signals are received simultaneously in parallel to produce ultrasonic information. During operation, transmitting/receiving conditions are selected from a plurality of transmitting/receiving conditions. Operation is then switched at a predetermined period between the selected transmitting/receiving conditions so that the three dimensional space is scanned by ultrasonic beams and echo signals are alternately received, at the predetermined period, under the selected transmitting/receiving conditions. Image information for each selected transmitting/receiving condition is obtained and respective ultrasonic images corresponding to each transmitting/receiving condition are simultaneously displayed.

11 Claims, 4 Drawing Sheets

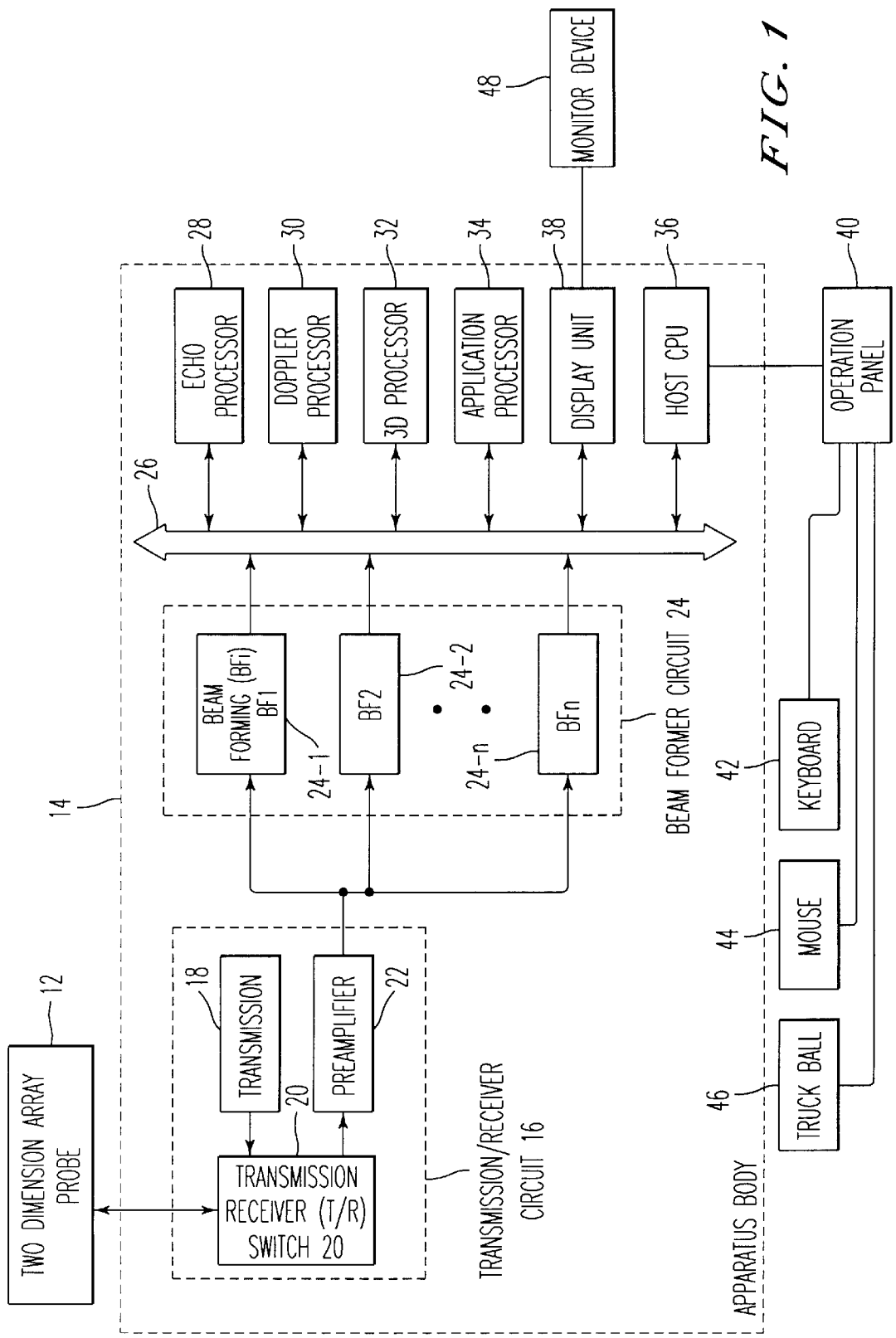

ULTRASONIC DIAGNOSTIC APPARATUS

CROSS REFERENCE TO RELATED APPLICATIONS

This application claims benefit of priority to Japanese Patent Application No. P10-292150 filed Oct. 14, 1998, the entire disclosure of which is incorporated by reference herein.

BACKGROUND OF THE INVENTION

1. Field of the Invention

The present invention relates to an ultrasonic diagnostic apparatus for displaying a three dimension ultrasonic image obtained by scanning a three dimensional space with ultrasonic beams.

2. Discussion of the Background

Recently, there has been developed a real time three dimension diagnostic apparatus for displaying ultrasonic information of a three dimensional space in real time by scanning the three dimensional space with ultrasonic beams. In the field, there is utilized a technique of electronically scanning a three dimensional space with ultrasonic beams, simultaneously receiving signals in parallel, displaying information on an optional cross sectional surface or three dimension information and simultaneously collecting ultrasonic echo signals from a plurality of directions by receiving beams in a plurality of directions in response to one transmitted ultrasonic beam in order to scan a desirable space in real time.

However, it is necessary to provide a transmitted ultrasonic beam having a wide width to receive signals in parallel simultaneously so that deterioration of transmitting sensitivity can not be avoided. In fact, the size of each element in a two dimension array probe would become 1/30 the size of each element in a conventional one dimension array probe. Therefore, the sound pressure of transmitted signals would be reduced and a S/N ratio of transmitting/receiving signals would be deteriorated.

The reduction of the sound pressure of the transmitting signals translates to a deterioration of the S/N ratio of a B-mode image (cross sectional image) and the problem of deteriorating color sensitivity becomes serious. Regarding a tissue harmonic mode and a contrast echo mode in which it is necessary to transmit signals at a sound pressure as high as possible, the reduction of the sound pressure is a serious problem. Regarding a real time three dimension ultrasonic diagnosis, it is required to have an image quality equal to or greater than that of a conventional B-mode ultrasonic diagnostic apparatus and to avoid deterioration of space analysis performance.

In the case of three dimension scanning in a parallel simultaneously receiving method, the directivity of elements, particularly in a sector type probe, has a adverse influence on the sensitivity of the apparatus.

In the conventional real time three dimensional ultrasonic diagnostic apparatus, a frame rate has been improved by widening a beam width of a transmitting beam and receiving echo signals from a plurality of directions simultaneously (number of simultaneously receiving signals transmitted in parallel is increased) in order to display a three dimensional image in real time by scanning a three dimensional space. Although the real time performance is improved by improving the frame rate, image quality is adversely influenced by deterioration of sensitivity, space analysis performance, the S/N ratio and a reduction of sound pressure. In the conventional parallel simultaneously receiving method, the sensitivity of a beam scanned in an oblique direction is more greatly deteriorated than that of a beam scanned in a direction perpendicular to an opening surface.

SUMMARY OF THE INVENTION

Accordingly, an object of the present invention is to provide an ultrasonic diagnostic apparatus for displaying in real time various ultrasonic information including a high quality cross sectional image based on cross sectional image data obtained by scanning a three dimensional space in real time.

Another object of the present invention is to provide an ultrasonic diagnostic apparatus which employs parallel simultaneous receiving, and in which sensitivity of a signal from a direction perpendicular to an aperture of a transducer and sensitivity of a signal from an oblique direction are substantially uniform.

These and other objects are achieved according to the present invention by providing a novel ultrasonic diagnostic apparatus for displaying ultrasonic information, wherein the ultrasonic information is obtained by scanning a three dimensional space with ultrasonic beams, and returned echo signals are subjected to parallel simultaneously receiving, including means for selecting a plurality of transmitting/receiving conditions wherein the number of signals simultaneously received in parallel is different in each condition, and means for switching at a desired period transmitting and receiving in the plurality of transmitting/receiving conditions, wherein various ultrasonic images are displayed based on ultrasonic information obtained from operation under the plurality of transmitting/receiving conditions.

In the above apparatus, a plurality of ultrasonic images of different quality can be displayed, while a three dimensional space is scanned in real time.

According to another aspect of the present invention, there is provided an ultrasonic diagnostic apparatus for scanning a three dimensional space with ultrasonic beams, receiving reflected echo signals and displaying ultrasonic information of the three dimensional space, including means for determining a first transmitting/receiving condition for scanning the whole three dimensional space and a second transmitting/receiving condition for scanning a specific region of the three dimensional space, means for alternately switching at a desired period transmitting and receiving between the first and second transmitting/receiving conditions, and means for displaying various ultrasonic images based on ultrasonic information obtained under the first and second transmitting/receiving conditions.

In the above apparatus according to the present invention, three dimensional image information can be obtained and displayed and fine image information of a predetermined region can also be obtained and displayed.

In an ultrasonic diagnostic apparatus according to the present invention as above described, the specific region scanned under the second transmitting/receiving condition is a cross sectional surface in an ultrasonic beam direction. Therefore, in the apparatus according to the present invention, three dimensional image information of an object and fine image information of a predetermined region of the object can be obtained and displayed.

According to a further aspect of the ultrasonic diagnostic apparatus according to the present invention, the first and second transmitting/receiving conditions can differ from each other in regard to at least one of sound pressure, a central frequency, bandwidth, and pulse cycles of a transmitted ultrasonic beam, an aperture size of transmission, transmitting focus point, a weighting function of a transmitting ultrasound on an aperture, and a central frequency and band of receiving ultrasonic beams, an aperture size at a receiving side, receiving focus point, a weighting function of a receiving ultrasound on an aperture, a raster density of transmitting/receiving signal and imaging modes (such as B mode, Doppler mode, and harmonic mode).

Therefore, a plurality of various images having different image quality can be obtained and displayed.

In one embodiment of the ultrasonic diagnostic apparatus according to the present invention as above described, the number of signals simultaneously received in parallel under the first transmitting/receiving condition is more than that in the second transmitting/receiving condition. Therefore, the whole three dimensional space can be properly scanned in real time under the first transmitting/receiving condition and a specific region can be finely scanned under the second transmitting/receiving condition. Furthermore, in this embodiment, a beam width of a transmitting beam in the second transmitting/receiving condition is narrower that in the first transmitting/receiving condition. Therefore, the specific region can be finely scanned under the second transmitting/receiving condition. Further, according to a further aspect of this embodiment, the second transmitting/receiving condition is a transmitting/receiving condition in a harmonic mode. Therefore, the second transmitting/receiving condition selects high sound pressure in order to improve a S/N ratio and image resolution. Alternatively, the second transmitting/receiving condition is a transmitting/receiving condition in a color Doppler mode. Therefore, the second transmitting/receiving condition selects high sound pressure in order to improve color sensitivity.

In another variation, the first transmitting/receiving condition is selected to have low sound pressure and the second transmitting/receiving condition is selected to have high sound pressure. Therefore, in the first transmitting/receiving condition, breaking of micro bubbles included in a contrast medium can be reduced to as little as possible. In the second transmitting/receiving condition, signals generated by breaking micro bubbles are effectively detected so that an image in a contrast echo mode can be obtained with high S/N ratio and high resolution, i.e., improved likelihood of detecting unusual or abnormal tissue.

In yet another embodiment of the ultrasonic diagnostic apparatus according to the present invention, the second transmitting/receiving condition is a multi transmitting method for transmitting ultrasonic beams toward the same direction at a plurality of times, with varying focus points.

Therefore, in the second transmitting/receiving condition, the specific region can be finely scanned at a short period.

According to another embodiment of the present invention, there is provided an ultrasonic diagnostic apparatus for scanning a three dimensional space with ultrasonic beams and obtaining ultrasonic information of the three dimensional space in the parallel simultaneously receiving method, wherein a scanning space of ultrasonic beams becomes narrower and/or the number of signals simultaneously received in parallel is decreased the farther a scanned point is away from a center line of the three dimensional space. Therefore, in this embodiment in obtaining ultrasound information, beam scanning in a central direction and beams scanning in an oblique direction have the same sensitivity.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a block diagram of a first embodiment of an ultrasonic diagnostic apparatus according to the present invention.

DETAILED DESCRIPTION OF THE PREFERRED EMBODIMENTS

Figure 2A:
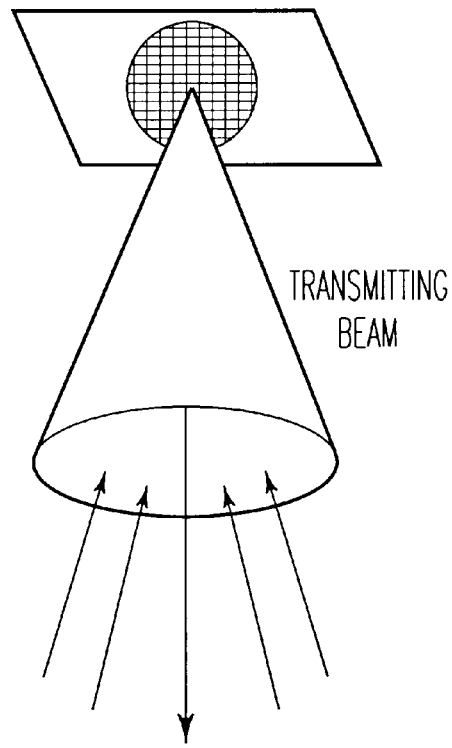
FIGS. 2(*a*) and 2(*b*) are sketches illustrating a transmitting/receiving condition of (a) a three dimensional real time wide scanning and (b) a fine scanning, respectively, in a first embodiment of the present invention.

Referring now to the drawings, wherein like reference numerals designate identical or corresponding parts throughout the several views, and more particular to FIG. 1 thereof, a first embodiment of a real time three dimensional ultrasonic diagnostic apparatus according to the present invention will be described.

First Embodiment

As shown in FIG. 1, a two dimensional array probe 12 includes a two dimensional array of piezoelectric transducers (i.e., 64 channels×64 channels=4,096 channels). A piezoelectric transducer in each channel is connected directly or indirectly to a body 14 through a switch provided at a probe case or a probe connector (not shown).

A transmission/receiver circuit 16 in the body 14 includes a transmission member 18 from which a transmission pulse having delay time selected for each channel corresponding to a transmission focus point is supplied to a respective piezoelectric transducer through a transmission/receiver (T/R) switch 20. The transmission pulse is converted to a sound pressure signal by the probe 12 and then the sound pressure signal is transmitted.

Echo signals from an object, such as a living body, are received at a predetermined channel selected in the probe 12 and amplified by a preamplifier 22. In beam former circuit 24, a delay time is added to the signal by means of plural beam forming elements (BFi) 24–i (i=1 to n) in each transmission direction in order to form a received beam corresponding to a desirable receiving focal point.

The beam former circuit 24 is connected to a system bus 26. An echo processor 28, a Doppler processor 30, a 3D processor 32, an application processor 34, a host CPU 36 and a display unit 38 are connected to the system bus 26. The echo processor 28 produces a B-mode cross sectional image corresponding to brightness of an echo signal. The Doppler processor 30 detects Doppler components in the echo signal in order to obtain blood flow information such as flow direction and speed of blood flow and then produces a color flow mapping image for displaying a color mapping image on the B-mode cross sectional image. The 3D processor 32 produces a three dimensional image such as a bird's-eye view based on three dimensional image information derived from a plurality of cross sections. The application processor 34 executes an applied measurement software and a three dimensional reconstruction software (dedicated hard web is also acceptable). For example, the applied measurement software automatically detects myocardium of a left ventricle from an image of the heart and calculates an amount of flowing blood based on the Doppler image. The host CPU 36 includes an instruction input device such as a keyboard 42, a mouse 44, a track ball 46 and so. Alternatively, an operation panel 40 is connected to the host CPU 36. A monitor device 48 is connected to the display unit 38.

An operation of the embodiment will be next described. Although the embodiment employs a parallel simultaneously receiving method, various transmitting/receiving conditions are acceptable by changing the number of signals simultaneously received in parallel. Transmitting/receiving conditions can be switched at a predetermined period. Usually, a three dimensional real time scanning for a three dimensional space is operated at a predetermined frame rate. Therefore, as shown in FIG. 2(*a*), a parallel simultaneously receiving technique for detecting received signals from a plurality of directions produced by a massive transmitted beam is utilized (in order to increase the number of signals simultaneously received in parallel). An operator designates a desired cross section along an ultrasonic beam by utilizing an instruction input device such as the keyboard 42, the mouse 44 and the track ball 46. Independent of the three dimensional scanning, at a predetermined time the designated cross section is finely scanned, as shown in FIG. 2(*b*), for example, with a transmitting beam which is narrow and in which the number of signals simultaneously received in parallel is decreased in order to detect a signal with high sensitivity and high analysis performance. In particular, a beam width in a slice direction perpendicular to a cross section is selected to have a suitable focus point and diameter to achieve high sensitivity. A raster space is smaller than three dimensional scanning space in some cases. A multi-transmitting method for transmitting beams toward a plurality of focus points several times is also selectable for the fine scanning. That is, an adjustment of the distance of the raster space in a direction of scanning is useful to improve resolution. It is preferable that sensitivity and resolution of the scanning with respect to a designated cross section is higher than those of scanning according to a conventional two dimensional ultrasonic apparatus. The sensitivity and resolution of the scanning according to the present invention can be improved by a weighting process on an aperture for transmitting and receiving signals in a region and selecting the most suitable focus point with respect to both of the scanning direction and the slice direction. In the three dimensional scanning, although an ultrasonic beam having relatively low frequency and experiencing low attenuation through an organ is used, where high sensitivity is preferred, a designated cross section is scanned with a beam under a different transmitting/receiving condition including high frequency beam irradiation in order to form a B-mode image with high resolution.

Figure 3:
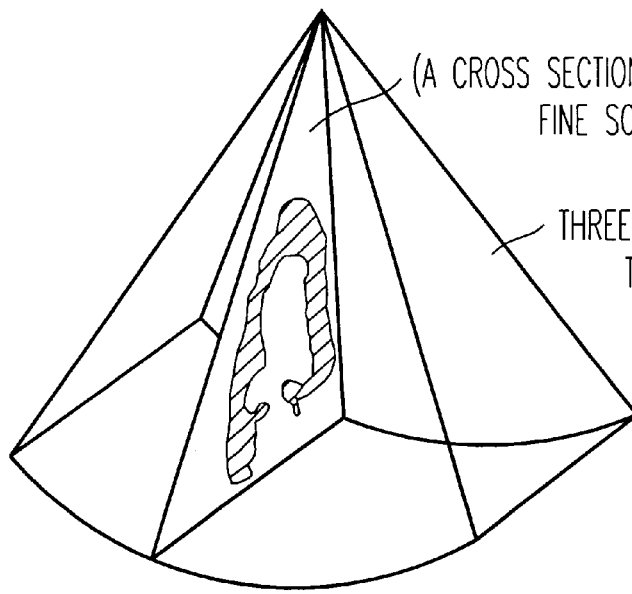
FIG. 3 is a sketch illustrating a scanning area of the three dimensional real time scanning and the fine scanning of the first embodiment.

FIG. 3 shows a relation between a scanning area of three dimensional real time scanning and a cross section for fine scanning. In FIG. 3, a three dimensional image is omitted, but a fine and high-resolution image is displayed on a designated cross section in an ultrasonic beam direction.

Figure 4:
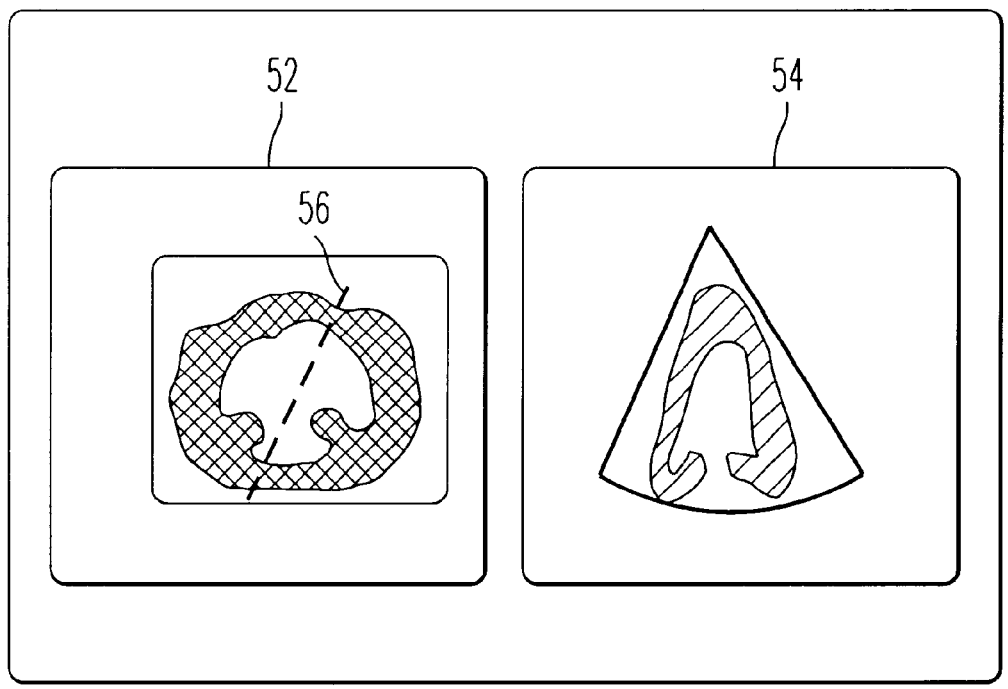
FIG. 4 is an illustration of one example of a picture of the three dimensional real time scanning and a picture of the fine scanning obtained in the first embodiment.

Regarding methods to display an image produced by the three dimensional real time scanning and a display of a cross sectional image produced by a fine scanning, many possible variations exist. For example, as shown in FIG. 4, an arbitrarily selected cross sectional image 52 shown from an arbitrarily selected direction and reconstructed based on information obtained by three dimensional scanning may be juxtaposed with a fine cross sectional image 54 appointed on a designated cross section of the image 52, with the images being displayed in real time. The cross sectional image 52 thus serves like a road map for selection of the cross sectional image 54, and a cross sectional line of the fine cross sectional image 54 is shown as a broken line 56 in the cross sectional image 52. Under such operation according to the present invention, if a position of the cross sectional line 56 is moved in accordance with an instruction from the instruction input device such as the keyboard 42, the mouse 44 and the track ball 46, a cross section of the fine scanning is independently correspondingly changed, as is the displayed fine cross sectional image 54. The image produced by the three dimensional real time scanning is not restricted to any particular cross sectional image 52, and on the contrary, a 3D image shown at any point of sight (for example, from an upper oblique direction) is possible. The image is reconstructed by the 3D processor 32.

As described above, according to the embodiment of the present invention, the three dimensional scanning is operated in real time while a transmitting/receiving condition for collecting ultrasonic information in three dimensional space and a transmitting/receiving condition for fine scanning with respect to a designated cross sectional surface are alternately switched at a predetermined switching period. For example, in the parallel simultaneously receiving method, frame rate and quality of image for fine scanning are controlled by changing the number of signals simultaneously received in parallel. In the three dimensional real time scanning, the parallel simultaneously receiving method is often utilized (to increase a number of signals simultaneously received in parallel) and the scanning is operated with low raster density in order to maintain the frame rate higher than a predetermined level (e.g., 20 Hz). On the other hand, with respect to a cross sectional surface for producing a fine image, the number of signals simultaneously received in parallel is decreased and the raster density is high.

Further, the present invention contemplates combining 1.5 dimensional scanning, an intermediate scanning method between one dimensional scanning and two dimensional scanning, and a harmonic imaging method. The one dimensional array uses a piezoelectric transducer array aligned in a lateral direction. The two dimensional array uses piezoelectric transducer array aligned in a lateral direction and a longitudinal direction. The 1.5 dimensional array uses a piezoelectric transducer array in which plural rows are aligned in a lateral direction and plural rows are aligned in a longitudinal direction. The number of rows in a lateral direction is almost the same as that of the one dimensional array, (e.g., 100 rows in a lateral direction×10 rows in a longitudinal direction). However, in the one dimensional array and the 1.5 dimensional array, ultrasonic beams scan a cross section. In the two dimensional array, ultrasonic beams scan three dimensional space freely. A difference between the one dimensional array and the 1.5 dimensional array is that piezoelectric transducers are aligned in a longitudinal direction in the 1.5 dimensional array so that ultrasonic beams in a slice direction can be controlled to a certain degree and the beam characteristic in the slice direction can be improved in order to produce an image. (By 1.5 dimensional scanning is meant that ultrasound beams scan a cross-section while controlling a beam in the slice direction.) If the present invention utilizing a two dimensional array probe is applied to the 1.5 dimensional scanning, a designated cross section is scanned in the second transmitting/receiving condition and the probe transducer array is controlled under the most suitable transmitting/receiving condition in order to control a beam in the slice direction. The tissue harmonic method is a method for designating one transmitting/receiving condition as one condition of fine scanning. If the harmonic method is used as the transmitting/receiving condition in conjunction with application of a contrast medium, the transmitting/receiving condition serves to detect contrast medium.

A three dimensional image or a cross sectional image along a desired line is displayed in real time based on two kinds of ultrasonic information and a fine cross sectional image is displayed in real time. Accordingly, information about three dimensional space is displayed in real time and a fine image about a region of interest is simultaneously displayed so that a diagnostic performance is remarkably improved by obtaining real time morphological or fine cross sectional image information at the specific region.

Second Embodiment

The second embodiment according to the present invention will be next described. Numbered elements of the second embodiment corresponding to those of the first embodiment have the same number and a detailed description thereof is omitted.

Figure 2B:
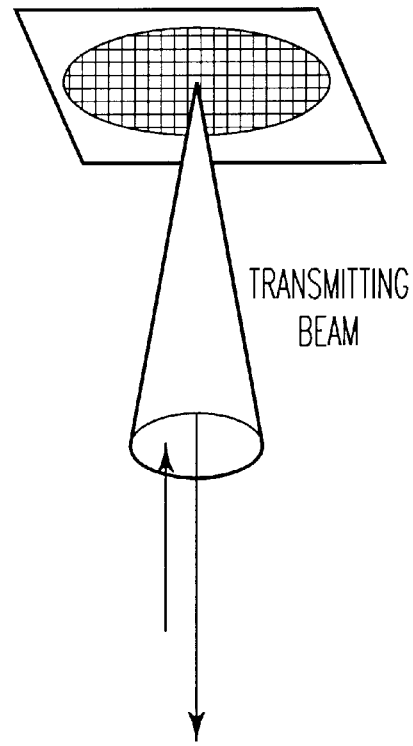

A block diagram of the second embodiment is substantially the same as that of the first embodiment. Therefore, the block diagram of the second embodiment is omitted. In the second embodiment, scanning modes are different from those of the first embodiment. In the first embodiment, the three dimensional real time scanning and the fine scanning are operated to obtain a B-mode cross sectional image. In the second embodiment, three dimensional scanning is operated for obtaining a B-mode image and a color Doppler image and fine scanning is operated with respect to a designated cross section in order to obtain a color Doppler image. Similar to the first embodiment, the three dimensional real time scanning utilizes a technique for simultaneously receiving signals in parallel, and to increase the number of simultaneously received signals in parallel for detecting received signals from a plurality of directions uses a massive transmitting beam as shown in FIG. 2(a). As shown in FIG. 2(b), as with the first embodiment, the fine scanning utilizes narrow beams. The transmitting/receiving condition of the fine scanning is selected to enhance performance for detecting a blood flow signal. The most suitable focus point is selected by considering transmitting/receiving frequency, diameter of a beam, and the most preferable focus point with respect to both of a scanning direction and a slice direction in order to produce a color Doppler cross sectional image having a quality which is equal to or greater than that of a conventional two dimensional ultrasonic apparatus.

Figure 5:
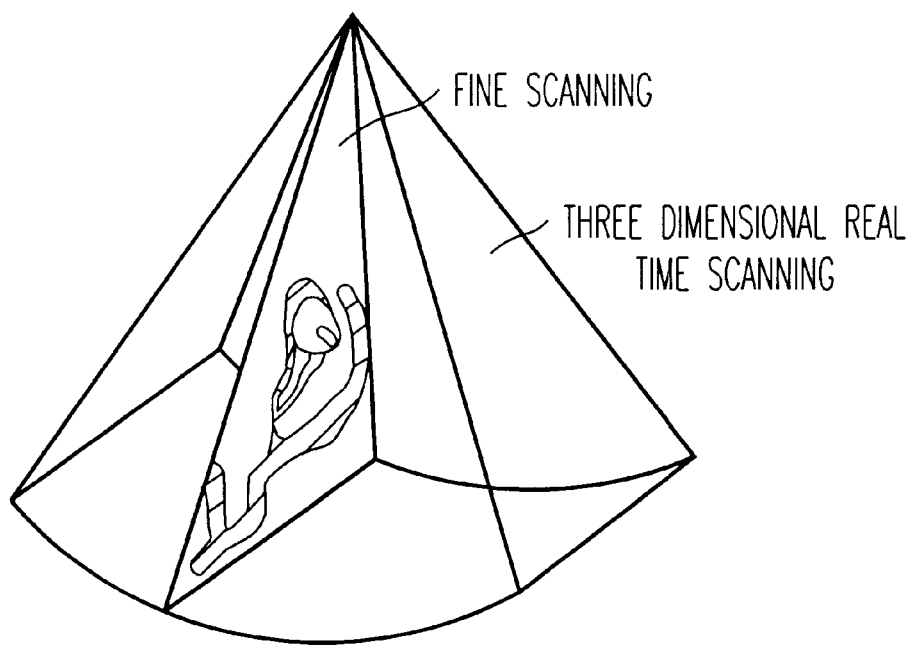
FIG. 5 is a sketch illustrating a scanning area of the three dimensional real time scanning and the fine scanning of color Doppler mode in a second embodiment according to the present invention.

FIG. 5 shows a relation between a scanning area of three dimensional real time scanning and a cross section of fine scanning. In FIG. 5, although a three dimensional image is omitted, a fine color Doppler image (blood flow image) with high sensitivity is displayed with high resolution on a cross section designated in an ultrasonic beam direction.

Variations of display in the second embodiment are the same as those of the first embodiment. As shown in FIG. 4, an arbitrarily selected cross sectional image in an arbitrarily selected direction and a fine cross sectional image on the designated cross section are juxtaposed. The images may be displayed in real time and the three dimensional picture and the fine cross sectional image on the designated surface may be juxtaposed.

In the second embodiment, while three dimensional space is scanned in real time, information of the three dimensional space is displayed in real time and a fine image about the region of interest is simultaneously displayed by collecting ultrasonic information of three dimensional space and scanning a designated cross section finely. Diagnostic performance is remarkably improved by obtaining real time morphological information in three dimensional space, or fine color Doppler information about the specific region.

Third Embodiment

A block diagram of the third embodiment is substantially the same as that of the first embodiment. Therefore, an explanation of numbered elements is omitted. The third embodiment relates to a contrast echo mode in which the transmitting/receiving condition of echo signals is varied by changing the sound pressure thereof. In three dimensional monitor scanning, three dimensional space is scanned in real time by utilizing a massive beam as shown in FIG. 2(a) so that echo signals having low sound pressure are produced to prevent breaking of micro bubbles included in a contrast medium. On a designated cross section, echo signals with high sound pressure are transmitted by utilizing a narrow beam as shown in FIG. 2(b) in order to detect signals from contrast medium (micro bubbles) with high sensitivity (flash or fine scanning). Transmitting/receiving condition of the flash scanning, particularly to a condition of a focus point, is considered with a distribution of sound pressure on the cross section and selects the most suitable condition with respect to both of a scanning direction and a slice direction in order to produce an image of a quality equal to or higher than that of the cross sectional image obtained in a conventional ultrasonic apparatus. In case of using contrast medium, it is preferable to transmit and receive signals based on the harmonic mode. Further, it is possible to employ the harmonic mode together with the Doppler mode (flash is performed in the Doppler mode or a harmonic Doppler mode).

Figure 6:
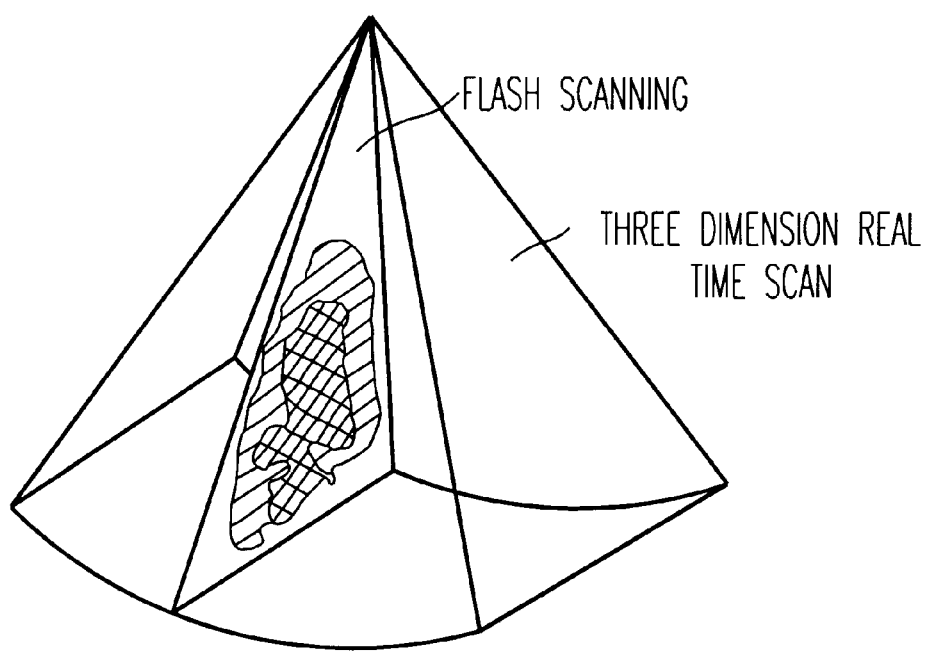
FIG. 6 is a sketch illustrating a scanning area of the three dimensional real time scanning and the fine scanning for contrast echo in a third embodiment according to the present invention.

FIG. 6 shows a relation between a scanning area of three dimensional real time scan and a cross sectional surface of flash scanning. Although the three dimensional image is omitted in FIG. 6, regarding a cross sectional image designated in an ultrasonic beam direction, a fine flash scanned image (intermittent fine image, that is, an image enhanced with contrast medium) with high sensitivity is displayed for high resolution.

Display variations of the third embodiment are the same as those of the first embodiment. As shown in FIG. 4, an arbitrarily selected cross sectional image from an arbitrarily selected direction and a fine flash scanning image on a designated cross section may be displayed in real time in juxtaposed relation.

In the third embodiment, while three dimensional space is scanned in real time, information of the three dimensional space is displayed in real time and a fine image at a region of interest is simultaneously displayed by receiving ultrasonic information in the three dimensional space and fine scanning a designated cross sectional surface so that a diagnostic performance can be remarkably improved by real time morphological information in three dimensional space, or fine contrast enhanced information of perfusion at the specific region.

In a modification example of the third embodiment, the designated cross section may be observed at a frame rate higher than that of three dimensional scanning while the most suitable sound pressure prevents bubbles from breaking at the designated cross section. Although display of a morphological image in real time and an enhanced image has been explained in the third embodiment, a three dimensional image enhanced with contrast medium is displayed in real time at a harmonic mode with low sound pressure and an intermittent fine flash image with high sensitivity and high resolution is displayed while breaking of bubbles is prevented.

The Fourth Embodiment

Figure 7:
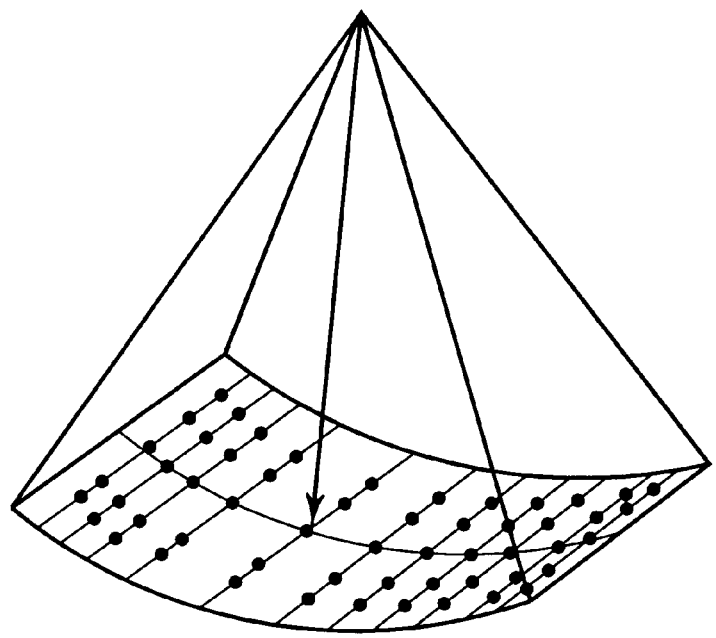
FIG. 7 is a sketch illustrating a scanning space changed in dependance on a direction of an ultrasonic beam in order to explain a principle of the fourth embodiment.

In the above described third embodiment, the number of signals simultaneously received in parallel, and the sound pressure thereof are uniformly changed. In the fourth embodiment, the transmitting/receiving condition is changed by each ultrasonic beam in a respective scanning direction. In the case of three dimensional scanning by the parallel simultaneously receiving method, the fourth embodiment compensates for deterioration of sensitivity influenced by directivity of an element when a beam is scanned in an oblique direction with respect to an aperture. As shown in FIG. 7, the scanning space of the ultrasonic beam becomes narrower with increased distance from the center line of three dimensional space in order to compensate for the deterioration of sensitivity by increasing raster density. In FIG. 7, points at a bottom surface of a pyramid for showing a three dimensional scanning area as shown in FIG. 7 indicate raster density, that is, crossing points of receiving raster and the bottom surface. In FIG. 7, the scanning space of the ultrasonic beam becomes narrower and the raster density 72 is increased. The transmitted beam in an oblique direction becomes narrower and a number of simultaneously receiving signals in parallel is decreased in order to improve its sensitivity.

In the parallel simultaneously receiving method, sensitivity in a central direction and sensitivity in an oblique direction are maintained at substantially the same level by changing raster density in a central direction in a three dimensional scanning and raster density in an oblique direction.

Although the invention has been explained in relation to its preferred embodiments, it is to be understood that many other possible modifications and variations can be made without departing from the spirit and scope of the invention. Although as a transmitting/receiving condition there has been described (1) a number of transmitting/receiving beams in parallel, (2) sound pressure, (3) central frequency, (4) bandwidth, waveform and/or pulse cycles, and (5) a transmitting aperture size, focus point and weighting function of a transmitting ultrasound on an aperture, in addition, (6) a receiving aperture size, (7) a receiving focus point, (8) a weighting function of a receiving ultrasound on an aperture and (9) at lease one mode of the above described modes (e.g., B mode, Doppler mode and harmonic mode) may be utilized as the transmitting/receiving condition. Features of the fourth embodiment may be combined with those of the other embodiments.

As described above, according to the present invention, an ultrasonic diagnostic apparatus in which an ultrasonic image in a three dimensional space or an optional cross sectional image in the three dimensional space is displayed as a road map. A cross sectional image of a desired cross section is displayed with a higher S/N ratio and higher resolution than those of a cross sectional image obtained by a conventional two dimensional ultrasonic diagnostic apparatus. Thus, information of the three dimensional space is displayed in real time and a high quality image about a region of interest is simultaneously displayed. Further, diagnostic performance is remarkably improved by obtaining a real time morphology of three dimensional space, and information of a high quality cross sectional image of the region. If the present invention is applied to a Doppler method, blood flow on a desired cross section can be detected with high sensitivity while a position of blood vessel is recognized in the three dimensional space. If the present invention is applied to a contrast echo mode, perfusion and enhanced blood vessel on a desired cross section can be obtained, while its morphology and tissue movement is observed in the three dimensional space.

Obviously, numerous modifications and variations of the present invention are possible in light of the above teachings. It is therefore to be understood that within the scope of the appended claims, the invention may be practiced otherwise than as specifically described herein.

What is claimed is:

1. An ultrasonic diagnostic apparatus wherein a three dimensional space is scanned by ultrasonic beams and echo signal are received to produce ultrasonic information, comprising:

means for transmitting ultrasonic beam and receiving ultrasonic echo at transmitting/receiving conditions;

means for switching the transmitting/receiving conditions between first condition for scanning three-dimensional space by wide width ultrasonic beam and second condition for scanning two-dimensional plane by the narrow width ultrasonic beam at a predetermined period;

means for generating raster data from echo signals by simultaneously parallel processing; and means for real-time and simultaneously displaying different ultrasonic images based on ultrasonic echo under respective of said transmitting/receiving conditions.

2. An ultrasonic diagnostic apparatus wherein a three dimensional space is scanned by ultrasonic beams and echo signals are received to produce ultrasonic information, comprising:

means for selecting a first transmitting/receiving condition for scanning the three dimensional space and a second transmitting/receiving condition for scanning a designated region of said three dimensional space;

means for switching at a predetermined period between the selected first and second transmitting/receiving conditions so that said three dimensional space is scanned by ultrasonic beams and echo signals received under the first transmitting/receiving condition and alternately said designated region of said three dimensional space is scanned by ultrasonic beams and echo signals received under the second transmitting/receiving condition to obtain respective ultrasound information; and means for displaying different ultrasonic images based on the respective ultrasonic information obtained under said first and second transmitting/receiving conditions.

3. The apparatus of claim 2, comprising means for designating a cross sectional surface in an ultrasonic beam direction as said designated region.

4. The apparatus of claim 1 or 2, wherein said means for selecting comprises means for selecting said transmitting/receiving condition from at least one of sound pressure, a central frequency, bandwidth, wave form and pulse cycles of a transmitted ultrasonic beam, an aperture size of a transmitting side, a transmitting focus point, a weighting function of a transmitting ultrasound on an aperture, a central frequency and band of a receiving ultrasonic beam, an aperture size at a receiving side, a receiving focus point, a weighting function of a receiving ultrasonic on an aperture, a raster density of transmitting/receiving signal, a Doppler mode, a harmonic mode and a B mode.

5. The apparatus of claim 2, wherein said selecting means comprises means for selecting a first number of signals simultaneously received in parallel in said first transmitting/receiving condition and a second number of signals simultaneously received in parallel in said second transmitting/receiving condition, wherein said first number is greater than said second number.

6. The apparatus of claim 5, wherein said selecting means comprises means for selecting a width of a transmitting beam in said second transmitting/receiving condition to be narrower than that in said first transmitting/receiving condition.

7. The apparatus of claim 5, wherein said selecting means comprises means for selecting the second transmitting/receiving condition as a transmitting/receiving condition in a harmonic mode.

8. The apparatus of claim 5, wherein said selecting means comprises means for selecting the second transmitting/receiving condition as a transmitting/receiving condition in a color Doppler mode.

9. The apparatus of claim 2, wherein said selecting means comprises means for selecting as said first transmitting/receiving condition a low sound pressure for preventing micro bubbles included in a contrast medium from breaking and as said second transmitting/receiving condition a high sound pressure for effectively detecting signals generated at a moment when micro bubbles are broken.

10. The apparatus of claim 2, wherein said selecting means comprises means for selecting as said second transmitting/receiving condition a multi transmitting method for transmitting ultrasonic beams toward the same direction at a plurality of times, with varying focus points.

11. An ultrasonic diagnostic apparatus wherein a three dimensional space is scanned by ultrasonic beams and echo signal are received to produce ultrasonic information, comprising:

a probe having two-dimensional array transducers for transmitting/receiving ultrasonic, a transmission circuit supplying a transmission pulse to the transducer to alternately scan the three-dimensional area by ultrasonic beam having wide width and two-dimensional area by the ultrasonic beam having narrow width, a beam former generating raster data from the ultrasonic echo signal from the transducer by parallel simultaneously receiving processing, a processor generating a display image based on the raster data, the display image is including an animated three-dimensional image corresponding to the wide width ultrasonic beam and high resolution two-dimensional image corresponding to the narrow width ultrasonic beam.

* * * * *